United States Patent [19]
Mooradian et al.

[11] Patent Number: 5,853,744
[45] Date of Patent: Dec. 29, 1998

[54] SOLID-PHASE METHOD FOR ATTACHING A BIOMOLECULE TO A SUBSTRATE SURFACE WITH A PHOTOREACTIVE CROSSLINKING AGENT

[75] Inventors: Daniel L. Mooradian, Eagan; Gregg B. Fields, Brooklyn Park, both of Minn.

[73] Assignee: Regents of the University of Minnesota, Minneapolis, Minn.

[21] Appl. No.: 699,965

[22] Filed: Aug. 20, 1996

[51] Int. Cl.$^6$ ................ A61F 2/06; C12N 5/00; C12N 11/06; C07K 17/06
[52] U.S. Cl. ............... 424/422; 435/174; 435/177; 435/180; 435/181; 435/395; 530/402; 530/810; 530/812; 530/815; 530/816
[58] Field of Search ................... 435/174, 177, 435/180, 181, 395; 530/402, 810, 812, 815, 816; 424/422

[56] References Cited

U.S. PATENT DOCUMENTS

| | | | |
|---|---|---|---|
| 4,973,493 | 11/1990 | Guire | 427/2 |
| 4,979,959 | 12/1990 | Guire | 623/66 |
| 5,117,009 | 5/1992 | Barany | 549/394 |
| 5,196,566 | 3/1993 | Barany et al. | 560/61 |
| 5,563,056 | 10/1996 | Swan et al. | 435/180 |

OTHER PUBLICATIONS

Barany et al., "Solid–Phase Peptide Synthesis", *The Peptides*, vol. 2, Title Page, Copyright Page, and Table of Contents (v–viii) (1980).

Albericio et al., "Preparation and Application of the 5–(4–(9–Fluorenylmethyloxy carbonyl)aminomethyl–3, 5–dimethoxyphenoxy)–valeric Acid (PAL) Handle for the Solid–Phase Sythesi of C–Terminal Peptide Amides under Mild Conditions", *J. Org. Chem.*, 55, 3730–3743 (1990).

Andrade et al., "The Contact Angle and Interface Energetics", *Surface and Interfacial Aspects of Biomedical Polymers*, vol. 1, 249–292 (1985).

Barany et al., "Solid–phase peptide sythesis: a silver anniversary report", *Int. J. Peptide Protein Res.*, 30, 705–739 (1987).

Diglio et al., "Rat Heart–Derived Endothelial and Smooth Muscle Cell Cultures: Isolation, Cloning and Characterization", *Tissue and Cell*, 20, 477–492 (1988).

C.G. Fields et al., "Edman Degradation Sequence Analysis of Resin–Bound Peptides Synthesized by 9–Fluorenylmthoxycarbonyl Chemistry", *Peptide Research*, 6, 39–47 (1993).

G.B. Fields et al., "Principles and Practice of Solid–Phase Peptide Synthesis", *Synthetic Peptides: A User's Guide* (G.A. Grant, Ed.), W.H. Freeman and Co., N.Y., Chapter 3, pp. 77–183, (1992).

G.B. Fields et al., "Solid phase peptide synthesis utiliing 9–fluorenylmethoxycarbonyl amino acids", *Int. J. Peptide Protein Res., 35* , 161–214 (1990).

Huebsch et al., "Endothelial Cell Interactions With Synthetic Peptides From the Carboxyl–Terminal Heparin–Binding Domains of Fibronectin", *Circ. Res., 77* , 43–53 (1995).

Huebsch, "Peptide/Biomaterial Hybrids as Substrates for Endothelial Cell Adhesion, Spreading, Motility, and Proliferation", *A Thesis Submitted to the Faculty of the Graduate School of the University of Minnesota* , Tittle Page, i–vii, 1–92 (Jan. 1995).

Huebsch et al., "Photoreactive analog of peptide FN–C/H__V from the carboxyterminal heparin–binding domains of fibronectin supports endothelial cell adhesion and spreading on biomaterial surfaces", *J. Biomed. Mat. Res.*, 31, 555–567 (1996).

Kaelble et al., "Interfacial Bonding and Environmental Stability of Polymer Matrix Composites", *J. Adhesion*, 6, 23–48 (1974).

Merrifield, "Solid Phase Peptide Synthesis. I. The Synthesis of a Tetrapeptide", *J. Am. Chem. Soc.*, 85, 2149–2154 (1963).

Sacher, "The Determination of the Surface Tensions of Solid Films", *Surface Characterization of Biomaterials* , B.D. Ratner, Ed., Elsevier, NY, pp. 53–64, (1988) (Proceedings of the Symposium on Surface Analysis of Biomaterials, Ann Arbor, MI, Jun. 2–24,1987).

H. Sigrist et al., "Light–Dependent, Covalent Immobilization of Biomolecules on 'Inert' Surfaces", *Bio/Technology*, 10, 1026–1028 (1992).

Wilke et al., "Human Keratinocytes Adhere to Two Distinct Heparin–Binding Synthetic Peptides Derived from Fibronectin", *J. Invest, Dermatol.*, 97, 573–579 (1991).

Yan et al., "Photochemical Functionalization of Polymer Surfaces and the Production of Biomolecule–Carrying Micrometer–Scale Structures by Deep–UV Lithography Using 4–Substituted Perfluorophenyl Azides", *J. Am. Chem. Soc.*,115, 814–816 (1993).

*Primary Examiner*—David M. Naff
*Attorney, Agent, or Firm*—Mueting, Raasch & Gebhardt, P.A.

[57] ABSTRACT

A method for making a medical device having a biomolecule immobilized on a substrate surface is provided. The method includes: providing an immobilized biomolecule comprising a biomolecule covalently attached to a support material; attaching a photoreactive crosslinking agent to the immobilized biomolecule to form a photoreactive analog of the biomolecule; and removing the photoreactive analog of the biomolecule from the support material. The photoreactive analog of the biomolecule can then be attached to a substrate surface, such as a biomaterial that forms part of a medical device. The immobilized biomolecule may contain a peptide having an $N^\alpha$-terminus. The photoreactive crosslinking agent is attached to the peptide at the $N^\alpha$-terminus to form the photoreactive analog of the biomolecule. The peptide can be an adhesion peptide containing the sequence Trp-Gln-Pro-Pro-Arg-Ala-Arg-Ile. Attachment of the peptide to a substrate surface promotes cell adhesion to the surface. The photoreactive crosslinking agent can be heterobifunctional or contain two photoreactive groups. The photoreactive analog of the biomolecule is attached to the substrate surface by activating a photoreactive group of the analog such as by exposing the analog to UV radiation.

23 Claims, 4 Drawing Sheets

SOLID-PHASE METHOD FOR ATTACHING A BIOMOLECULE TO A SUBSTRATE SURFACE WITH A PHOTOREACTIVE CROSSLINKING AGENT

BACKGROUND OF THE INVENTION

The implantation of medical devices (e.g., pacemakers, vascular grafts, stents, heart valves, etc.) that contact bodily tissues or fluids is a rapidly developing area of medicine. A major problem with such devices is that their surfaces tend to adsorb a layer of proteins from tissues and fluids such as tears, urine, lymph fluid, blood, blood products, etc. The composition and organization of this adsorbed protein layer is thought to influence further biological reactions. Adverse biological reactions such as thrombosis and inflammation can diminish the useful lifetime of many devices.

For example, the long term patency of small caliber (<6 mm) synthetic vascular grafts is typically poor. The early failure of these grafts is commonly due to thrombosis at the blood-biomaterial interface while subsequent failures are generally due to intimal hyperplasia and stenosis. It has been hypothesized that the establishment of a functional endothelial cell layer on the surface of vascular grafts as a result of autologous endothelial seeding prior to implantation, or as a result of the migration and proliferation of endothelial cells from the graft anastomosis, would lead to reduced thrombogenicity and hyperplasia, and therefore improved patency. However, the biomaterials commonly used as vascular grafts are poor substrates for endothelial cell attachment, migration, and proliferation.

The extracellular matrix is recognized as a regulator of cellular adhesion, spreading, and motility. Therefore, the use of extracellular matrix proteins to manipulate the molecular-level surface properties of implanted vascular graft biomaterials may provide an opportunity to directly influence endothelial cell interactions with vascular graft surfaces. As an example, vascular grafts have been precoated with extracellular matrix proteins, such as fibronectin and laminin, in an attempt to increase endothelial cell adhesion.

Figure 1:
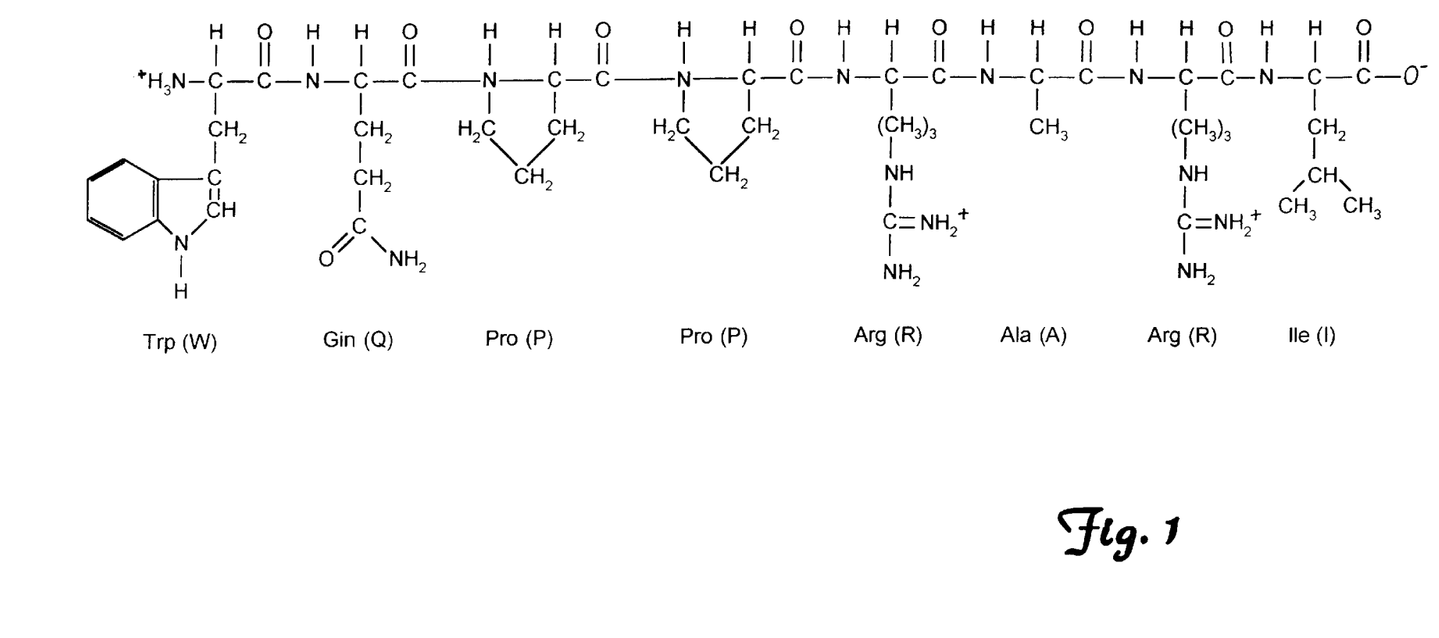
FIG. 1. Chemical structure of adhesion-promoting peptide FN-C/H-V (SEQ ID NO:2) from the 33/66 kD carboxyl-terminal heparin-binding fragments of fibronectin.

Studies on the molecular basis of cell adhesion to extracellular matrix proteins have identified several peptide sequences which contribute to the adhesion-promoting activity of these proteins. These sequences include Tyr-Ile-Gly-Ser-Arg (YIGSR) (SEQ. ID NO:1) from laminin and Arg-Gly-Asp (RGD), which is present in many extracellular matrix proteins, including fibronectin. Adhesion promoting peptides such as YIGSR (SEQ. ID NO:1) and RGD have been used as alternatives to intact laminin and fibronectin (FN) in the surface modification of biomaterials. However, the 33/66 kD carboxyl-terminal heparin-binding fragments of fibronectin molecule also support the adhesion of various cell types, including human umbilical vein endothelial cells. A peptide sequence within the 33/66 kD FN fragments, FN-C/H-V, which is shown in FIG. 1 and has the sequence Trp-Gln-Pro-Pro-Arg-Ala-Arg-Ile (WQPPRARI) (SEQ ID NO:2), that promotes the adhesion, spreading, and migration of endothelial cells has been identified from various sources. See, Huebsch et al., *Circ. Res.*, 77(1), 43–53 (1995). Thus, the sequence defined by the peptide FN-C/H-V (SEQ. ID NO:2) may be useful as an alternative to intact fibronectin (FN) for surface modification of vascular biomaterials.

Peptide surface modification has typically relied on chemical methods to covalently immobilize the synthetic peptides to the biomaterial surface. Biomolecules such as growth factors, cell attachment proteins, and cell attachment peptides have been used for this purpose. In addition, biomolecules such as antithrombogenics, antiplatelets, anti-inflammatories, antimicrobials, and the like have also been used to minimize adverse biomaterial-associated reactions. Approaches to attaching such biomolecules to a biomaterial surface typically require the use of coupling molecules such as glutaraldehyde, cyanogen bromide, p-benzoquinone, succinic anhydrides, carbodiimides, diisocyanates, ethyl chloroformate, dipyridyl disulphide, epichlorohydrin, among others. These techniques are usually complex, however, requiring functionalization of both the peptide and the biomaterial prior to immobilization.

In contrast, aryl azides, which form highly reactive nitrenes upon exposure to UV light, form covalent linkages with a diverse set of chemical bonds (C—H, C—C, C—O, C—N, etc.). These compounds are now among the most commonly used photoreactive reagents. Applications of aryl azide-based methods have included uses in the photoimmobilization of biomolecules for receptor-ligand interaction research and in the development of biosensors and biomaterials. However, conventional aryl azide-based photoimmobilization methods typically require the initial attachment of the photoreactive reagent to the biomaterial with subsequent attachment of the biomolecule, or initial reaction of the photoreactive reagent with the biomolecule in solution with subsequent attachment of the resultant complex to the biomaterial. These conventional methods, however, require the use of large amounts of the biomolecules and/or involve difficult purification techniques.

Thus, a need exists for additional methods that have general utility for the coupling of biomolecules to biomaterial surfaces, particularly peptides that promote cell attachment, that are generally easier and more efficient than conventional methods.

SUMMARY OF THE INVENTION

The present invention provides a solid-phase method of generating a photoreactive analog of a biomolecule, the method comprising: providing an immobilized biomolecule comprising a biomolecule covalently attached to a support material; attaching a photoreactive crosslinking agent to the immobilized biomolecule to form an immobilized photoreactive analog of the biomolecule; and removing the photoreactive analog of the biomolecule from the support material. The photoreactive crosslinking agent is preferably a heterobifunctional photoreactive crosslinking agent and the biomolecule is preferably a peptide, more preferably an adhesion-promoting peptide (the resultant complex is therefore a photoreactive analog of an adhesion-promoting peptide). Preferably, the method involves synthesizing the biomolecule directly on the support material, although the biomolecule can be synthesized in whole or in part prior to attachment to the support material.

The present invention also provides a solid-phase method of modifying a substrate surface to include a biomolecule, the method comprising: providing an immobilized biomolecule comprising a biomolecule covalently attached to a support material; attaching a photoreactive crosslinking agent to the immobilized biomolecule to form an immobilized photoreactive analog of the biomolecule; removing the photoreactive analog of the biomolecule from the support material; and attaching the photoreactive analog of the biomolecule to a substrate surface. The step of attaching the photoreactive analog of the biomolecule to a substrate surface preferably comprises: contacting the photoreactive analog of the biomolecule to a substrate surface; and exposing the photoreactive analog of the biomolecule to UV radiation. Preferably, the substrate is a biomaterial, which preferably forms a part of a medical device, such as a vascular graft.

The present invention also provides a method for making a medical device comprising a biomaterial having a biomolecule thereon, the method comprising: providing an immobilized biomolecule comprising a biomolecule covalently attached to a support material; attaching a photoreactive crosslinking agent to the immobilized biomolecule to form an immobilized photoreactive analog of the biomolecule; removing the photoreactive analog of the biomolecule from the support material; and attaching the photoreactive analog of the biomolecule to the biomaterial by contacting the photoreactive analog of the biomolecule to the biomaterial, and exposing the photoreactive analog of the biomolecule and biomaterial to UV radiation.

Also provided is a method of promoting cell adhesion to a biomaterial, the method comprising: providing an immobilized adhesion-promoting peptide comprising an adhesion-promoting peptide covalently attached to a support material; attaching a photoreactive crosslinking agent to the immobilized peptide to form an immobilized photoreactive analog of the adhesion-promoting peptide; removing the photoreactive analog of the adhesion-promoting peptide from the support material; and attaching the photoreactive analog of the adhesion-promoting peptide to a biomaterial; and contacting cells to the biomaterial with the adhesion-promoting peptide thereon.

Also provided is a medical device comprising a biomaterial to which is covalently attached an adhesion-promoting peptide having the sequence Trp-Gln-Pro-Pro-Arg-Ala-Arg-Ile (WQPPRARI) (SEQ ID NO:2).

As used herein, "biomaterial" is defied as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and/or flexibility required to function for the intended purpose; can be purified, fabricated and sterilized easily; will substantially maintain its physical properties and finction during the time that it remains implanted in or in contact with the body.

As used herein, a "medical device" is a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like which are placed into the blood vessels or the heart for purposes of monitoring or repair.

DETAILED DESCRIPTION OF THE INVENTION

The present invention provides a solid-phase method of generating a complex of a photoreactive crosslinking agent and a biomolecule (preferably, a complex of a heterobifunctional photoreactive crosslinking agent and a biomolecule), which is herein referred to as a photoreactive analog of a biomolecule. This photoreactive analog of a biomolecule can be used to modify a substrate surface, such as a biomaterial surface of a medical device. Specifically, the present invention provides a solid-phase method for generating photoreactive analogs of adhesion-promoting peptides that can be covalently coupled to a variety of surfaces using UV light. Significantly, the resultant bound analogs retain their biological activity (e.g., promoting vascular endothelial cell adhesion and spreading).

The present invention also provides a method of modifying a substrate surface with a biomolecule by first providing an immobilized biomolecule comprising a biomolecule covalently attached to a support material (e.g., a polymeric resin), subsequently attaching a photoreactive crosslinking agent (e.g., a heterobifunctional photoreactive crosslinker) to the immobilized biomolecule to form an immobilized photoreactive analog of the biomolecule, removing the photoreactive analog of the biomolecule from the support material, and then attaching the photoreactive analog of the biomolecule to a substrate surface using conventional means (such as long wavelength (e.g., 360 nm) UV light).

Preferred methods of the present invention take advantage of solid-phase organic synthesis techniques of the biomolecules (e.g., peptides) to control the coupling (preferably, chemical coupling involving, for example, an acylation reaction) of a crosslinking agent (i.e., crosslinker) to the immobilized biomolecule. The use of solid-phase synthesis also simplifies the separation of the resulting immobilized biomolecule/crosslinker complex (i.e., the immobilized photoreactive analog of the biomolecule) from unwanted by-products, such as any unreacted crosslinking agent.

Although the biomolecules can be prepared by other methods and then attached to the support material for subsequent coupling with the crosslinking agent, it is preferred that standard solid-phase organic synthesis techniques, such as solid-phase peptide synthesis (SPPS) techniques be used. That is, a biomolecule such as a peptide can be synthesized, subsequently attached to a support material, coupled with a photoreactive crosslinking agent, and then removed from the support material using a variety of techniques. Preferably, however, the biomolecule is synthesized on the support material, coupled with a photoreactive crosslinking agent, and then removed from the support material using a variety of techniques.

For the preparation of peptides (oligopeptides, polypeptides, or proteins), solid-phase peptide synthesis involves a covalent attachment step (i.e., anchoring) that links the nascent peptide chain to a support material (typically, an insoluble polymeric support) containing appropriate functional groups for attachment. Subsequently, the anchored peptide is extended by a series of addition (deprotection/coupling) cycles that involve adding $N^\alpha$-protected and side-chain-protected amino acids stepwise in the C to N direction. Once chain assembly has been accomplished, protecting groups are removed and the peptide is cleaved from the support. Typically, the crosslinking agent is added to the peptide before the protecting groups are removed.

Typically, SPPS begins by using a handle to attach the initial amino acid residue to a functionalized support material. A handle (i.e., linker) is a bifunctional spacer that, on one end, incorporates features of a smoothly cleavable protecting group, and on the other end, a functional group, often a carboxyl group, that can be activated to allow coupling to the functionalized support material. Known handles include acid-labile p-alkoxybenzyl (PAB) handles, photolabile o-nitrobenzyl ester handles, and handles such as those described by Albericio et al., *J. Org. Chem.*, 55, 3730–3743 (1990) and references cited therein, and in U.S. Pat. Nos. 5,117,009 (Barany) and 5,196,566 (Barany et al.).

For example, if the support material is prepared with amino-functional monomers, typically, the appropriate handles are coupled quantitatively in a single step onto the amino-functionalized supports to provide a general starting point of well-defined structures for peptide chain assembly. The handle protecting group is removed and the C-terminal residue of the $N^\alpha$-protected first amino acid is coupled quantitatively to the handle. Once the handle is coupled to the support material and the initial amino acid or peptide is attached to the handle, the general synthesis cycle proceeds. The synthesis cycle generally consists of deprotection of the $N^\alpha$-amino group of the amino acid or peptide on the support material, washing, and, if necessary, a neutralization step, followed by reaction with a carboxyl-activated form of the next $N^\alpha$-protected amino acid. The cycle is repeated to form the peptide of interest. Solid-phase peptide synthesis methods using functionalized insoluble support materials are well known. See, for example, Merrifield, *J. Am. Chem. Soc.*, 85,2149 (1963); Barany and Merrifield, In Peptides, Vol. 2, pp. 1–284 (1979); Barany et al., *Int. J. Peptide Protein Res.*, 30, 705–739 (1987); Fields et al., In *Synthetic Peptides: A User's Guide* (G. A. Grant, Ed.), Chapter 3, pp. 77–183, W. H. Freeman and Co., NY (1992); and Fields et al., Int. *J. Peptide Protein Res.*, 35, 161–214 (1990).

When SPPS techniques are used to synthesize the peptides on the support material, Fmoc methodologies are preferably used. This involves the use of mild orthogonal techniques using the base-labile $N^\alpha$-9-fluorenylmethyloxycarbonyl (Fmoc) protecting group. Fmoc amino acids can be prepared using fluorenylmethyl succinimidyl carbonate (Fmoc-OSu), Fmoc chloride, or [4-(9-fluorenylmethyloxycarbonyloxy)phenyl] dimethylsulfonium methyl sulfate (Fmoc-ODSP). The Fmoc group can be removed using piperidine in dimethylformamide (DMF) or N-methylpyrrolidone, or using 1,8-diazabicyclo[5.4.0]undec-7-ene (DBU) in DMF. After Fmoc removal, the liberated $N^\alpha$-amine of the supported peptide is free and ready for immediate attachment of the photoreactive crosslinking agent, for example, without an intervening neutralization step. The immobilized photoreactive analog of the desired peptide can then be removed, for example, using trifluoroacetic acid (TFA) at room temperature. Such Fmoc solid-phase peptide synthesis methodologies are well known to one of skill in the art and are discussed in Fields et al., In *Synthetic Peptides: A User's Guide* (G. A. Grant, Ed.), Chapter 3, pp. 77–183, W. H. Freeman and Co., NY (1992); and Fields et al., *Int. J. Peptide Protein Res.*, 35, 161–214 (1990).

The methods of the present invention are exemplified herein by the generation of a photoreactive analog of an adhesion-promoting peptide from fibronectin (FN-C/H-V); however, it is applicable to other adhesion-promoting peptides as well. In this specific example, sulfosuccinimidyl 2-(p-azidosalicylamido) ethyl-1,3'-dithio-propionate (SASD), a crosslinking agent having a photoreactive aryl azide group and a chemically reactive ester group, is coupled to immobilized peptide FN-C/H-V (SEQ ID NO:2) through an acylation reaction. This insures that coupling occurs via the α-amino group (as opposed to the ε-amino group of lysine that may be present in the peptide of interest), under conditions (e.g., excess SASD) that favor complete conversion of the peptide FN-C/H-V to its photoreactive analog (referred to herein as ASD-V), and greatly simplifies the subsequent purification of the photoreactive peptide ASD-V. This photoreactive peptide can be attached to a substrate surface by activating the aryl azide group and forming a highly reactive nitrene group upon exposure to UV light. Significantly, when covalently coupled to a substrate surface (e.g., polystryrene (PS) or polyethlene terephthalate (PET)), the photoreactive peptide ASD-V retains its ability to promote the adhesion and spreading of endothelial cells, thereby demonstrating the utility of this method in applications where re-endothelialization is desired.

This approach represents an extension of the solid-phase synthesis of FN-C/H-V itself and involves the attachment of photoactive SASD to the $N^\alpha$-amino terminus of resin-bound peptide FN-C/H-V and the subsequent separation of unreacted SASD from resin-bound SASD-peptide. This approach differs substantially from the approach taken by others who use photoreactive crosslinkers to couple biomolecules to surfaces.

For example, Yan et al., *J. Am. Chem. Soc.*, 5, 814–816 (1993) have modified polymer surfaces using photoreactive N-hydroxysuccinimide-functionalized (NHS) perfluorophenyl azides (PFPAs). This is a two-step process in which the crosslinker is photoimmobilized onto the substrate prior to the covalent coupling of the peptide to the crosslinker. An alternate method is disclosed in U.S. Pat. Nos. 4,973,493 (Guire) and 4,979,959 (Guire). These methods suffer from at least two major disadvantages.

First, when soluble peptides are coupled to the reactive ester group of an immobilized crosslinker, the coupling may occur via ε-amino groups (i.e., as in lysine) within the peptide, as well as, α-amino groups. These residues may be part of the peptide's active site. Thus, crosslinking in this manner may have a deleterious effect on peptide function. In contrast, the addition of the bifunctional crosslinker to the resin-bound peptide, as is done in the method of the present invention, can be carried out before ε-amino groups have been deprotected. This insures that the coupling will occur exclusively at the amino-terminus of the peptide.

Second, the methods of Yan and Guire are generally wasteful of the biomolecules, as they are typically required in excess amounts. In contrast, in the method of the present invention, the maximal yield of coupled biomolecule is obtained under conditions in which the crosslinker is present in great excess and can thus drive the reaction in the appropriate direction. This condition is easily met when the biomolecule is bound to a support material, and the concentration of crosslinker can be varied as desired. It cannot easily be met when the concentration of the crosslinker is limited by its density on a surface as required by the methods of Yan and Guire.

Generally, biomolecules used according to this invention can be, for example: antibacterial and antimicrobial agents; anticoagulant and antithrombotic agents; platelet agents; anti-inflammatories; enzymes; catalysts; hormones; growth factors; drugs; vitamins; antibodies; antigens; nucleic acids; dyes (which act as biological ligands); DNA and RNA segments; and natural and synthetic cell attachment peptides or adhesion-promoting peptides. As long as the molecules can be immobilized on a support material they can be used in the method of the present invention. Preferably, suitable biomolecules for use in the method of the present invention are those capable of being synthesized on a support material, preferably using SPPS techniques, and more preferably Fmoc SPPS techniques. Specific examples of such biomolecules include peptides containing up to about 20 amino acid residues, typically about 8–20 amino acid residues. A particularly preferred peptide is FN-C/H-V, which is shown in FIG. 1 and has the sequence Trp-Gln-Pro-Pro-Arg-Ala-Arg-Ile (WQPPRARI) (SEQ ID NO:2).

Generally, suitable photoreactive crosslinking agents are those that include a first reactive group for attachment to an immobilized biomolecule, and a second reactive group that is photoreactive for attachment of the biomolecule to a substrate surface. The first reactive group can be photoreactive or chemically reactive, as long as it is reactive under different conditions than that of the second reactive group. Preferably, the first reactive group is chemically reactive and the second reactive group is photoreactive, thereby forming a heterobifunctional photoreactive crosslinker. That is, the first reactive group reacts under chemical conditions that do not activate the second reactive group, which allows for the attachment of the crosslinker to an immobilized biomolecule. Preferably, the second reactive group is activated by actinic radiation (typically long wavelength UV light), which allows for attachment of the crosslinker/biomolecule complex to a substrate surface. Typically, the crosslinkers used herein have two reactive groups per molecule (i.e., they are bifunctional), however, they can be multifunctional.

Preferably, the crosslinkers have at least one photoreactive group per molecule and at least one chemically reactive group per molecule. The photoreactive groups include, but are not limited to: nitrene generators such as aryl, alkyl, and acyl azides, oxazidines, and isocyanates; carbene generators such as alkyl and 2-ketodiazo derivatives and diazirines; triplet oxygen generators such as aromatic ketones; as well as carbonium ion and radical generators. The chemically reactive groups include, but are not limited to: ester groups, amino groups, carboxyl groups, halo groups, hydroxy groups, thiol groups, and isothiocyanate groups. Examples of such crosslinkers are disclosed in U.S. Pat. Nos. 4,973,493 (Guire) and 4,979,959 (Guire). A particularly desirable crosslinker is sulfosuccinimidyl 2-(p-azidosalicylamido) ethyl-1,3'-dithio-propionate (SASD), which has a photoreactive aryl azide group and a chemically reactive ester group. Other specific examples include commercially available photoreactive amino acids.

A variety of support materials for immobilization of the biomolecules can be used. They can be of inorganic or organic materials and can be in a variety of forms (e.g., membranes, particles, spherical beads, fibers, gels, glasses, etc.). Examples include, porous glass, silica, polystyrene, polydimethylacrylamides, cotton, paper, and the like. Examples of suitable support materials are described by Fields et al., *Int. J. Peptide Protein Res.*, 35, 161–214 (1990) and *Synthetic Peptides: A User's Guide* (G. A. Grant, Ed.), Chapter 3, pp. 77–183, W. H. Freeman and Co., NY (1992). Functionalized polystyrene, such as amino-functionalized polystyrene, aminomethyl polystyrene, aminoacyl polystyrene, p-methylbenzhydrylamine polystyrene, or polyethylene glycol-polystyrene resins can be used for this purpose.

The substrates that can be modified by the methods of the present invention include metals such as titanium/titanium alloys, TiNi (shape memory/super elastic), aluminum oxide, platinum/platinum alloys, stainless steels, MP35N, elgiloy, haynes 25, stellite, pyrolytic carbon, silver or glassy carbon; polymers such as polyamides, polycarbonates, polyethers, polyesters, polyolefins including polyethylenes or polypropylenes, polystyrenes, polyurethanes, polyvinyl chlorides, polyvinylpyrrolidones, silicone elastomers, fluoropolymers, polyacrylates, polyisoprenes, polytetrafluoroethylenes; minerals or ceramics such as hydroxyapatite; human or animal protein or tissue such as bone, skin, teeth, collagen, laminin, elastin or fibrin; organic materials such as wood, cellulose, or compressed carbon; and other materials such as glass, rubber, or the like. Substrates made using these materials can be coated or uncoated, and derivatized or underivitized.

The methods of the invention can be used to modify substrates of any shape or form including tubular, sheet, rod and articles of proper shape for use in a number of medical devices such as vascular grafts, aortic grafts, arterial, venous, or vascular tubing, vascular stents, dialysis membranes, tubing, or connectors, blood oxygenator tubing or membranes, ultrafiltration membranes, intra-aortic balloons, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind.

The invention will be further described by reference to the following detailed examples. These examples are offered to further illustrate the various specific and illustrative embodiments and techniques. It should be understood, however, that many variations and modifications may be made while remaining within the scope of the present invention.

EXAMPLES

Materials and Methods

Endothelial Cell Culture:

Rat heart endothelial cells (RHE-1A), previously shown by Huebsch et al., *Circ. Res.*, 77(1), 43–53 (1995) to attach and spread on peptide FN-C/H-V from the 33/66 kD carboxyl-terminal heparin-binding domains of fibronectin, were used in this study. These cells were isolated as described in Diglio et al., *Tissue and Cell*, 20, 477–492

(1988). RHE-1A cells exhibited a typical endothelial cell cobblestone morphology and positive immunofluorescent staining for the factor VIII-related antigen. RHE-1A cells were maintained in Dulbecco's modified eagles medium (DMEM) containing 10% fetal bovine serum. Cell cultures were incubated at 37° C. in an atmosphere of 5% $CO_2$ in air and the medium was changed three times weekly. RHE-1A cells were subcultured every 4 days at a split ratio of 1:5 using 5% trypsin+0.5% EDTA (Sigma Chemical Co., St. Louis, Mo.). RHE-1A cells were used between passage 8 and 10.

Synthesis and Characterization of ASD-V:

FN-C/H-V (FIG. 1) was synthesized at the Biomedical Engineering Center (University of Minnesota) on an Applied Biosystems 431A peptide synthesizer using Fmoc solid-phase protocols described in Fields et al., *Peptide Res.*, 6, 39–46 (1993). FN-C/H-V composition was verified by amino acid analysis prior to use. Its purity was greater than 95% based on analytical $C_{18}$ reversed-phase high performance liquid chromatography (RP-HPLC).

Figure 2:
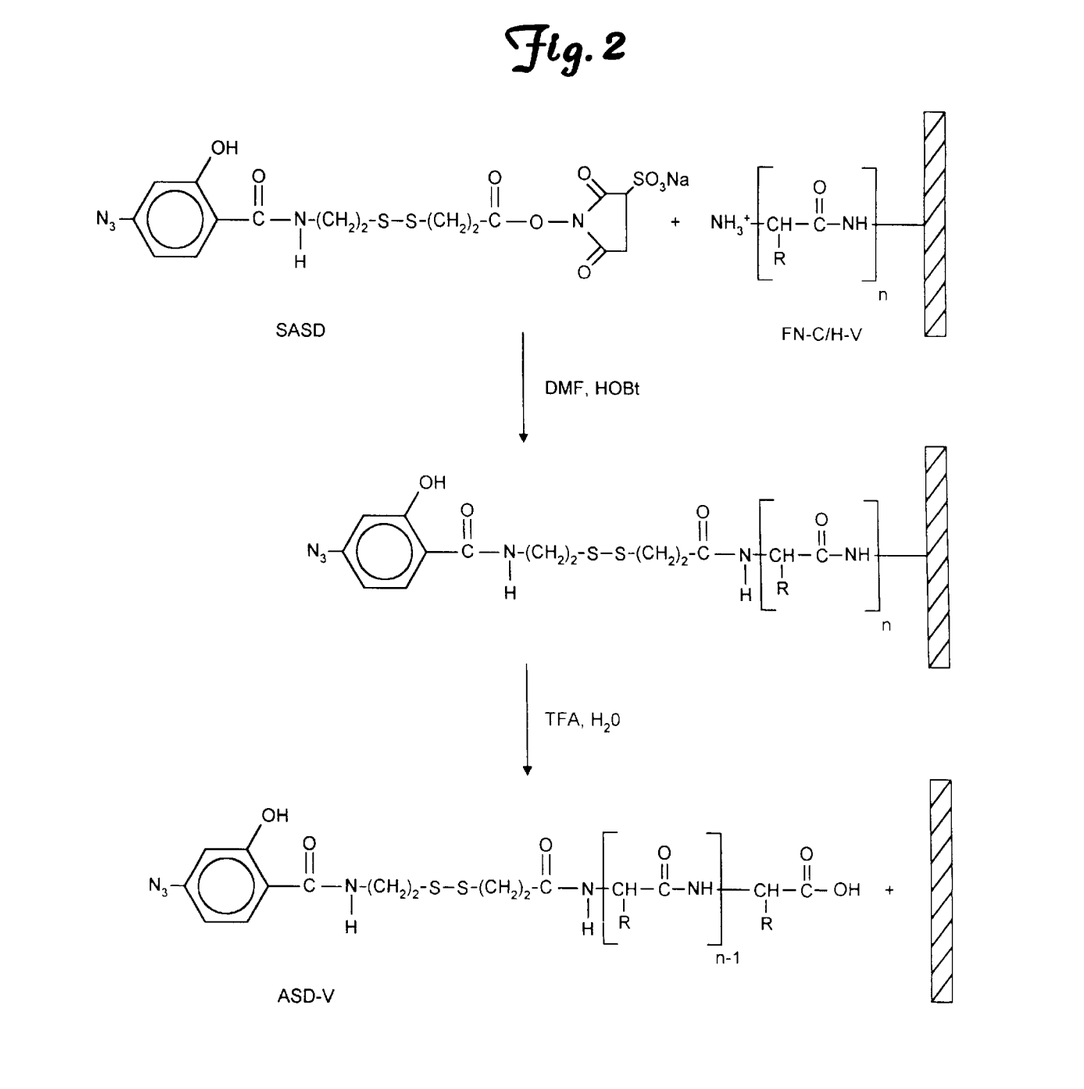
FIG. 2. Solid-phase synthesis of the photoreactive peptide, ASD-V.

Sulfosuccinimidyl 2-(p-azidosalicylamido)ethyl-1,3'-dithio-propionate (Pierce, Rockford, Ill.) (SASD) has a photoreactive aryl azide group and a chemically reactive sulfo-N-hydroxysuccinimide (NHS) ester group. ASD-V was generated by reacting FN-C/H-V with SASD as described in FIG. 2.

In a reaction vessel, 50 mg of SASD (0.0923 mmol) and 12.5 mg of N-hydroxybenzotriazole (HoBt) (0.0923 mmol) (Novabiochem, La Jolla, Calif.) were dissolved in 5 ml of N,N-dimethyl formamide (DMF). Resin bound FN-C/H-V (0.0462 mmol) was added to the reaction vessel, and the formation of ASD-V was allowed to proceed by shaking for four hours at room temperature. The reaction mixture was filtered through a sintered glass fimnel and the resin was washed three times with 20 ml each of DMF. Completion of the reaction between SASD and FN-C/H-V was verified by a ninhydrin reaction as described in Fields et al., *Peptide Res.*, 6, 39–46 (1993). The resin-bound ASD-V was then washed three times with 20 ml of dichloromethane. The product, a 2-(p-azidosalicylamido) ethyl-1,3'-dithio-propionate derivative of FN-C/H-V (ASD-V), was cleaved from the resin by the addition of 5 ml trifluoroacetic acid (TFA) in $H_2O$ (19:1 v/v) to the reaction vessel followed by shaking for two hours at room temperature. ASD-V was filtered through a sintered glass finnel, resuspended in $H_2O$, frozen and then lyophilized. All procedures were carried out under subdued lighting and all reaction vessels were covered with aluminum foil. ASD-V was characterized using fast atom bombardment mass spectrometry (FABMS) and RP-HPLC as described in Fields et al., *Peptide Res.*, 6, 39–46 (1993).

Preparation of $^{125}$I-ASD-V:

ASD-V was radiolabeled using IODO-GEN™ (Pierce, Rockford Ill.). Briefly, 0.5 mCi of $Na^{125}I$ (ICN) was injected into a sealed 2.0 ml Reacti-Vial which had been coated with 1 mg IODO-GEN™. One hundred micrograms of ASD-V was then added and incubated for 5 minutes at room temperature with frequent gentle mixing. Labeled ASD-V was loaded onto a Sep-Pak $C_{18}$ sample preparation cartridge (Waters Chromatography, Milford Mass.) rinsed with 5 ml acetonitrile and reequilibrated with 15 ml $H_2O$. The cartridge was washed with 50 ml phosphate buffered saline (PBS, pH=7.4) and then $H_2O$ until the radioactivity in the washes returned to baseline levels (<1500 dpm). $^{125}$I-ASD-V was then eluted from the Sep-Pak $C_{18}$ column with 60% acetonitrile 0.1% TFA. The radioactive samples were counted on a Gammatrac 1193 gamma counter (TM Analytical, Inc. Elk Grove Village, Ill.).

Contact angle measurements on ASD-V modified PS and PET:

Static and dynamic contact angle measurements were made using a telemicroscope and goniometer eyepiece (Gaertner Scientific, Chicago, Ill.) at 20° C. Drop volume was in the range 0.5–1.0 μl and drop application was controlled using a microsyringe. Surface energies were calculated using Kaelble's method (Kaelble et al., *J. Adhesion*, 6, 23–48 (1974)) using water, glycerol, formamide, ethylene glycol and n-dodecane. The overall approach and the calculations used to derive the surface energies are described elsewhere (Sacher, In *Surface Characterization of Biomaterials*, B. D. Ratner, Ed., Elsevier, N.Y., pp. 53–64 (1988)). ASD-V-modified ($PS_{uv}$ and $PET_{uv}$) and control ($PS_c$ and $PET_c$) surfaces were analyzed.

Advancing and receding contact angle (CA) measurements were also taken. These were used to calculate dynamic angle hysteresis for each surface, which is an estimate of surface roughness (Andrade et al., In *Surface and Interfacial Aspects of Biomedical Polymers. Surface Chemistry and Physics*, Vol. 1 J. D. Andrade, Ed., Plenum Press, NY, pp. 249–292 (1985)). Ten samples of each surface were analyzed. The precision of these contact angle measurements was ±2° for individual samples.

Atomic Force Microscopy:

The effects of peptide coupling on the surface properties of PS and PET were examined using an atomic force microscope (Nanoscope III, Digital Instruments, CA). The surface profiles of $PS_{uv}$, $PET_{uv}$, $PS_c$, and $PET_c$ were obtained, as were measurements of surface mean roughness (Roughness), standard deviation of the height values (RMS), and the range of height values (Z-range). Surface mean roughness is the mean value of the surface height relative to the center plane of the surface.

Quantitation of ASD-V immobilized to PS and PET:

The effect of several variables on the efficiency of ASD-V photocoupling to PS and PET were examined. These variables were pre-adsorption time, initial ASD-V coating concentration and UV irradiation time.

Fifty microliters of ASD-V in 0.1 M sodium phosphate buffer (pH=7.4) was added in triplicate to bacteriological grade polystyrene (PS) wells (Dynatech Laboratories, Inc., Chantilly, Va.) or 6 mm disks of 12 μm thick poly(ethylene terephthalate) (PET) (Mylar, DuPont Company, Wilmington, Del.) and allowed to adsorb at 37° C. for various time periods. The concentrations of ASD-V used in this study ranged from 0.1 to 100 nmol/ml. ASD-V adsorption time varied from 15 minutes to 24 hours. Following adsorption, PS and PET samples were irradiated with long wavelength UV light (355 nm) at room temperature (Blak-Ray, Ultra-Violet Products, Inc., San Gabriel, Calif. model XX15) from a distance of 3 cm for times ranging from 1 to 15 minutes. Material surfaces were subsequently washing three times (20 minutes each) with 0.1% Triton X100 to remove residual, non-covalently bound ASD-V. Materials treated in this manner are referred to as $PS_{uv}$ or $PET_{uv}$.

Corresponding controls consisted of PS and PET treated in an identical fashion except that they were not UV irradiated. This PS and PET is referred to as $PS_{ad}$ or $PET_{ad}$. Material samples not receiving any treatment are referred to as $PS_c$ or $PET_c$. Surface concentrations are expressed in picomoles of peptide coupled per unit area ($cm^2$).

Endothelial Cell Adhesion to ASD-V immobilized on PS and PET:

Endothelial cells were grown to 70–80% confluence in 75 $cm^2$ polystyrene flasks and labeled with $^{35}$S-methionine (10 μCi/ml) (Trans $^{35}$S-label, ICN Radiochemicals, Irvine, Calif.) for 24 hours. $PS_{uv}$, $PS_{ad}$, $PS_c$, $PET_{uv}$, $PET_{ad}$, and $PET_c$ surfaces were prepared as described above and blocked with a solution of 500 μg/ml ovalburnin in sodium phosphate buffer for 2 hours at 37° C. to eliminate nonspecific cell adhesion to PS and PET.

Subconfluent endothelial cells were harvested using trypsin: EDTA and resuspended in basal medium containing 10% FBS. The cells were centrifuged and resuspended twice in basal medium, counted and resuspended in basal medium containing 500 μg/ml ovalbumin at a final cell density of $5\times10^4$ cells/ml. 100 μl aliquots of this cell suspension were added to $PS_{uv}$, $PS_{ad}$, $PS_c$, $PET_{uv}$, $PET_{ad}$, and $PET_c$ surfaces and incubated at 37° C. in a 5% $CO_2$/air incubator. After 1 hour, non-adherent cells were removed by washing three times with basal medium (200 μl/well). Following washing, lysis buffer (1% SDS/0.5 N NaOH) was then added (100 μl) to each well. Following cell lysis (30 minutes at 60° C.) the contents of each well was transferred to a scintillation vial containing 5 ml EcoLite™ scintillation cocktail (ICN, Irvine, Calif.) and 0.1 ml water, and the radioactivity in each vial was measured in a Beckman 3801 scintillation counter.

Endothelial Cell Spreading on ASD-V immobilized on PS and PET:

Adherent RHE-1A cells were fixed with 3.6% formaldehyde (pH=7.0) in PBS after a 2 hour adhesion assay, performed as described above, and stained for 2 hours with Coomassie Brilliant Blue R-250. The cells were viewed on a Nikon Diaphot phase-contrast microscope with a 40× objective. Data (spread area) were collected from no fewer than 100 cells using OPTIMAS™ (BioScan Inc., Edmonds, Wash.) and a value for mean cell area was derived.

Samples to be examined by scanning electron microscopy (SEM) were fixed for 3 hours in a 5% glutaraldehyde/PBS (pH=7.0) solution at room temperature after a 2 hour adhesion assay performed as described above. The samples were then dehydrated in a series of graded ethanols, and dried in a critical point dryer (Tousimis Autosamdri model 814) using liquid $CO_2$ as the transition fluid. Samples were then coated with platinum using an EMS 76M sputter coater, examined with a Hitachi S-450 SEM at an accelerating voltage of 5 KV and photographed.

Results

Characterization of ASD-V:

The formation of ASD-V from the reaction of SASD with resin-bound FN-C/H-V was confirmed by $C_{18}$-RP-HPLC and FABMS. $C_{18}$-RP-HPLC analysis was monitored at three wavelengths (220, 254, and 280 nm). The $C_{18}$-RP-HPLC elution profile of ASD-V showed a single species with a retention time of 27 minutes at each of the wavelengths monitored (220 nm, 254 nm, and 280 nm). This confirms that the amide bonds of FN-C/H-V and ASD-V (220 nm), as well as the aromatic groups (254 and 280 nm) characteristic of SASD and tryptophan can be attributed to a single chemical species. FABMS analysis of ASD-V indicated the presence of two species with $[M+H]+=1347.6$ and 1111.6 Da. The 1347.6 Da species corresponds to the ASD-V species (calculated $[M+H]^+=1347.6$ Da). The 1111.6 Da species corresponds to a fragment resulting from the cleavage of the disulfide bond in ASD-V, and is most likely induced by FAB ionization since no corresponding peak was observed by $C_{18}$-RP-HPLC.

Effect of pre-adsorption time and UV irradiation time on ASD-V Immobilization to PS and PET:

The coupling of ASD-V to PS and PET was found to be independent of UV irradiation time in the range of 1 to 15 minutes. A one minute UV irradiation time was therefore used in subsequent experiments.

Figure 3A:
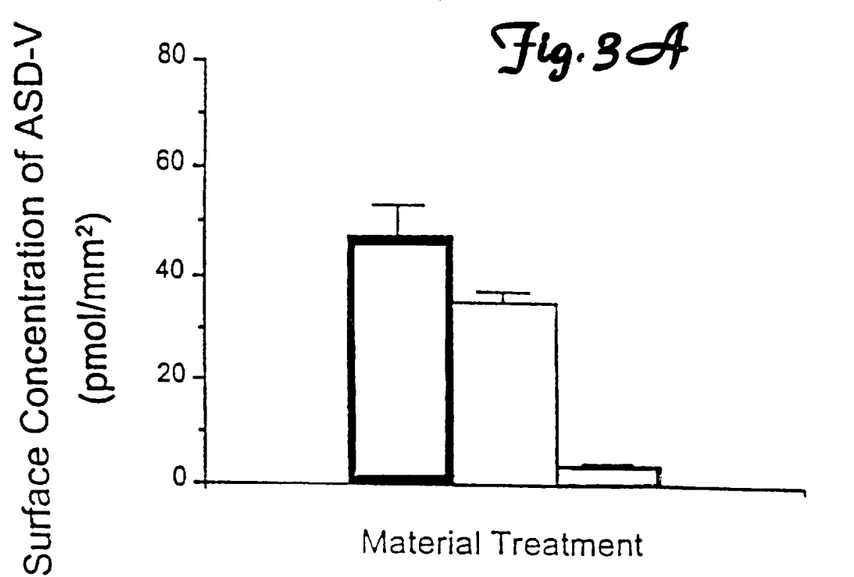
FIG. 3A. Coupling and retention of ASD-V by polystyrene (PS) following UV irradiation and Triton X-100 washing.
Figure 3B:
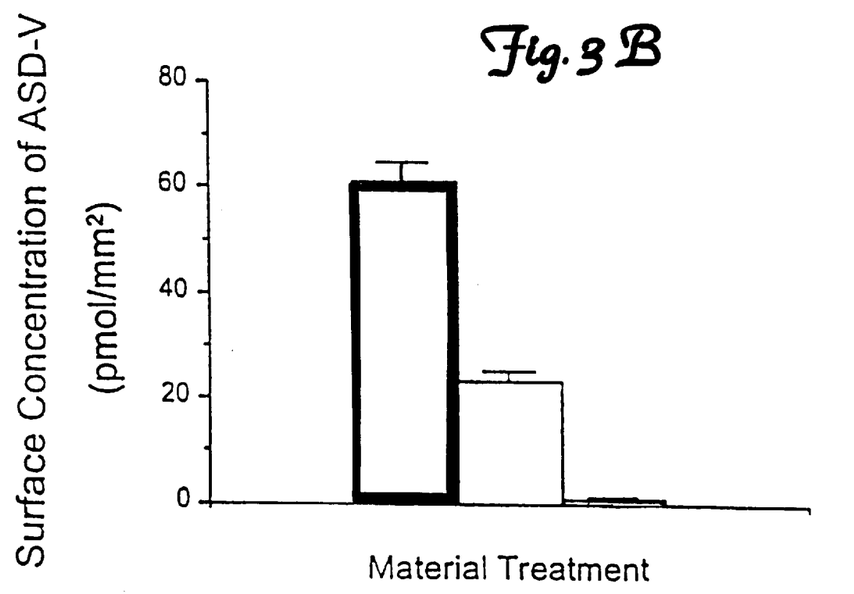
FIG. 3B. Coupling and retention of ASD-V by polyethylene terephthalate (PET) following UV irradiation and Triton X-100 washing. Surface concentration after 24 hours pre-adsorption of 100 nmol/ml ASD-V (Filled Bars). ASD-V retained after 1 minute UV irradiation and washing with 0.1% Triton X100 (Open Bars). ASD-V retained after adsorption followed by washing with 0.1% Triton X100 without UV irradiation (Shaded Bars). The coupling of radiolabeled ASD-V to PS and PET was measured as described under the Materials and Methods section. Data represent the mean ± one standard deviation, n=3.

After a 24 hour pre-adsorption, ASD-V surface concentration on PS and PET reached values of 47.6 pmol/mm² and 61.1 pmol/mm², respectively (FIG. 3). When these surfaces were washed with 0.1% Triton X100, very little of the ASD-V adsorbed to PS (3.9 pmol/mm²) and PET (1 pmol/mm²) surfaces remained (FIG. 3). In contrast, when PS and PET were exposed to UV irradiation following pre-adsorption with ASD-V, but prior to washing with 0.1% Triton X100, ASD-V surface concentrations were 35.15 pmol/mm² and 23.03 pmol/mm², respectively (FIG. 3). The values obtained following adsorption, UV irradiation and subsequent washing therefore represent the quantity of ASD-V covalently bound to the material surface.

The effect of pre-adsorption time on the extent of ASD-V coupling to PS and PET was subsequently examined. ASD-V coupling increased as a function of pre-adsorption time, reaching its highest point for $PS_{uv}$ and $PET_{uv}$ surfaces of 35.15 pmol/mm² and 23.03 pmol/mm², respectively, after a 24 hour pre-adsorption. The coupling of ASD-V to PS and PET was also dependent upon peptide concentration in the range of 0.1 to 100 nmol/ml although the coupling of ASD-V to PS or PET did not reach a maximum in this concentration range.

Static Contact Angle (CA) measurements and Surface energy calculation:

Surface energies were calculated for $PS_c$, $PS_{uv}$, $PET_c$ and $PET_{uv}$, using static contact angle measurements, and are shown in Table 1, below. Dispersive ($\gamma_d$) and polar ($\gamma_p$) contributions were determined using Kaelble's method and were used to calculate the overall surface energy ($\gamma_t$) for each sample. These measurements indicate that both PS and PET are predominately dispersive (i.e., hydrophobic). Interestingly, PS surfaces become more hydrophobic following peptide coupling, while PET surfaces become less hydrophobic.

TABLE 1

Dispersive ($\gamma_d$) and Polar ($\gamma_p$) Contributions to Total ($\gamma_s$) Surface Energy of $PS_c$, $PS_{uv}$, $PET_c$ and $PET_{uv}$

| Material | $\gamma_d$ | $\gamma_p$ (dynes/cm) | $\gamma_s$† | $R^2$ |
|---|---|---|---|---|
| $PS_c$ | 36.2 | $1.56 \times 10^{-2}$ | 36.2 | 0.653 |
| $PS_{uv}$ | 30.3 | $2.03 \times 10^{-2}$ | 30.3 | 0.914 |
| $PET_c$ | 27.5 | $2.61 \times 10^{-2}$ | 27.5 | 0.837 |
| $PET_{uv}$ | 34.6 | $2.26 \times 10^{-2}$ | 34.6 | 0.802 |

†$\gamma_d + \gamma_p = \gamma_s$

As seen in Table 2, below, contact angle hysteresis on PS decreases following peptide coupling (21° vs 8° for $PS_c$ and $PS_{uv}$, respectively) but increases on PET following peptide coupling (12° vs 24°, for $PET_c$ and $PET_{uv}$, respectively). Contact angle hysteresis is a useful measure of surface roughness, and these findings therefore suggest that the roughness of PS surfaces increases following peptide coupling, while the roughness of PET surfaces decreases following peptide coupling.

TABLE 2

Characterization of PS/PET surfaces by Dynamic Contact Angle Measurement and Atomic Force Microscopy

| | Contact Angle (degrees) | | | AFM parameters [Mean (nm)] | | |
|---|---|---|---|---|---|---|
| | Advancing | Receding | Hysteresis | RMS[a] | Roughness[b] | Z-range[c] |
| $PS_c$ | 75 | 54 | 21 | 5.71 | 4.27 | 49.0 |
| $PS_{uv}$ | 91 | 83 | 8 | 12.13 | 8.65 | 277.96 |
| $Pet_C$ | 46 | 34 | 12 | 22.59 | 14.10 | 444.32 |
| $PET_{uv}$ | 93 | 69 | 24 | 13.12 | 9.50 | 137.42 |

[a]RMS = Standard deviation of height values.
[b]Roughness = Surface mean roughness.
[c]Z-range = Range of height values.

Characterization of surface roughness by atomic force microscopy (AFM):

AFM images of $PS_c$, $PS_{uv}$, $PET_c$ and $PET_{uv}$ surfaces were evaluated. The $PS_c$ surfaces were relatively smooth, displaying gradual, dull convolutions. Following the covalent coupling of ASD-V, surfaces were clearly rougher, the previously identified dull convolutions obscured by heterogeneous peaks representing covalently coupled ASD-V. In contrast, PET surfaces were quite rough. Following ASD-V coupling a decrease in PET roughness was evident.

Surface mean roughness of PS increased following ASD-V coupling (4.274 nm vs 8.647 nm, for $PS_c$ and $PS_{uv}$, respectively), while the surface mean roughness of PET decreased following ASD-V coupling (14.103 nm vs 9.496 nm, for $PS_c$ and $PS_{uv}$, respectively). These results are consistent with the changes in surface roughness predicted by contact angle hysteresis calculations.

Figure 4A:
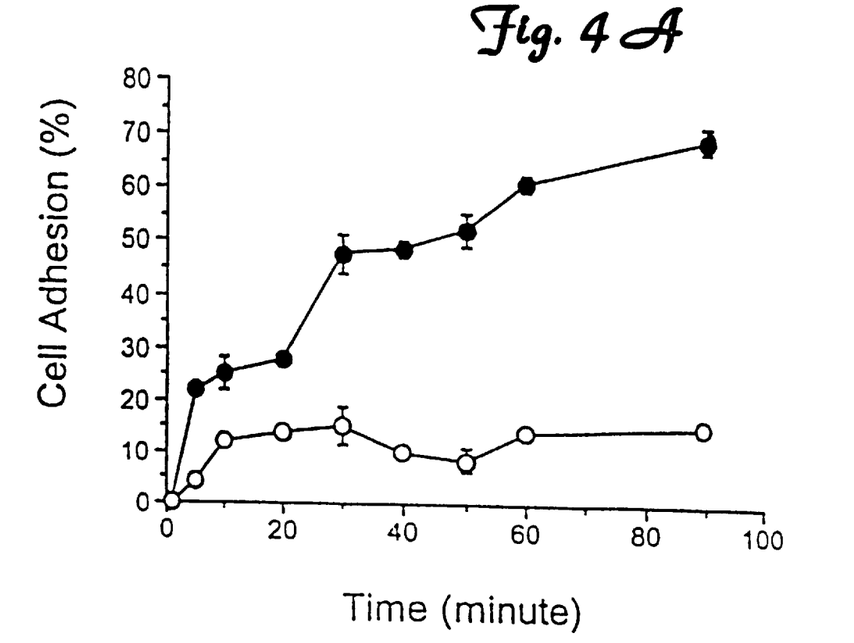
FIG. 4A. Endothelial cell adhesion to ASD-V modified (filled circles) and unmodified (open circles) PS.
Figure 4B:
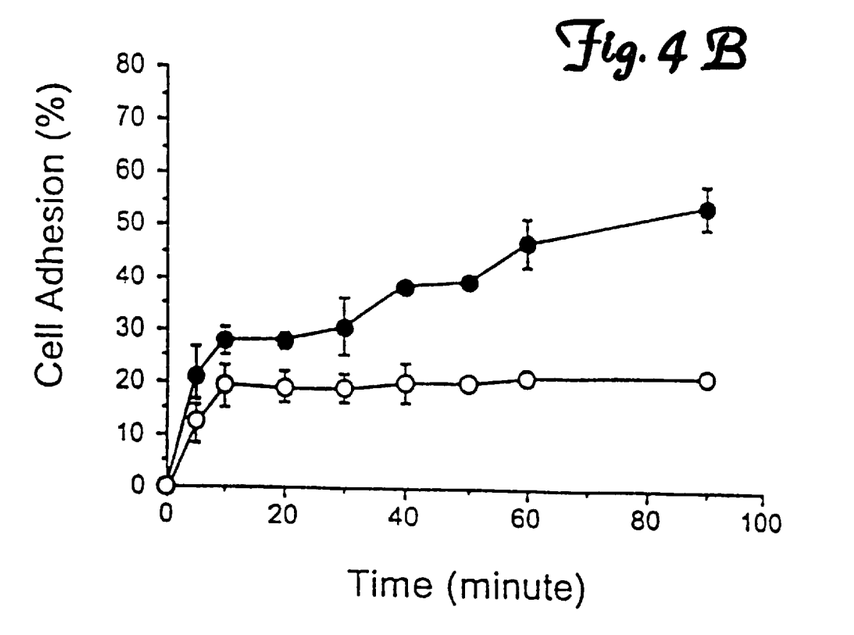
FIG. 4B. Endothelial cell adhesion to ASD-V modified (filled circles) and unmodified (open circles) PET. Endothelial cells were seeded onto PS and PET as described under the Materials and Methods section. All surfaces blocked with 0.5 mg/ml ovalburnin (OVA) for two hours. Endothelial adhesion was measured after 90 minutes. Data represent the mean ± one standard deviation, n =3.

Endothelial cell adhesion to ASD-V immobilized on PS and PET:

FN-C/H-V has previously been shown to promote the adhesion of vascular endothelial cells from a variety of sources, including RHE-1A cells, as disclosed by Wilke et al., *J. Invest. Dermatol.*, 97, 573–579 (1991). Therefore, whether ASD-V, when coupled to PS and PET, would retain its biological activity, was evaluated. RHE-1A adhesion to $PS_{uv}$ increased in a time-dependent manner reaching a maximum of 67% after 90 minutes (FIG. 4A). In contrast, cell adhesion to $PS_c$ (FIG. 4A), and to PS surfaces modified with SASD alone was significantly lower. RHE-1A adhesion to $PET_{uv}$ also increased in a time-dependent manner reaching a maximum of 54% after 90 minutes (FIG. 4B). Cell adhesion to $PET_c$ (FIG. 4B), and to PET surfaces modified with SASD alone was substantially lower.

Endothelial cell spreading on ASD-V immobilized on PS and PET:

RHE-1A cells seeded on $PS_{uv}$ were well spread within two hours and had an average spread area of 1400±624 $\mu m^2$/cell. In contrast, RHE-1A cell spreading on $PS_c$ (average spread area 144±109) was accompanied by little or no spreading, as was RHE-1A adhesion to PS surfaces modified with SASD alone. RHE-1A cells seeded on $PET_{uv}$ were also well spread, with an average spread area of 1133±567 $\mu m^2$/cell. There was limited spreading by RHE-1A cells on $PET_c$ surfaces (average surface area 259±124 $\mu m^2$/cell) and PET surfaces modified with SASD.

Discussion of Results

Coupling of ASD-V to PS and PET resulted in surface concentrations of 35.15 pmol/$mmm^2$ and 23.03 pmol/$mm^2$, respectively, being obtained after a 24 hour pre-adsorption. These surface concentrations correspond to an ASD-V coupling efficiency of 4.85% for coupling to PS and 3.18% for coupling to PET.

The changes in surface energy after ASD-V surface modification are consistent with the changes observed in surface roughness using AFM and the changes in contact angle hysteresis. Interestingly, the ASD-V coupling raises the surface energy of $PET_{uv}$, while lowering the surface energy of $PS_{uv}$. This may be attributed-in part-to differences in the initial roughness of PS and PET, and also to the presence of peptide aggregates that were found in greater number on the surfaces of $PS_{uv}$ than on $PET_{uv}$.

RHE-1A cell adhesion to the ASD-V modified PS and PET surfaces increased in a time-dependent manner, reaching a maximum of 67% and 54%, respectively, after 90 minutes. These results are comparable with previous work using ovalbumin-coupled FN-C/H-V, as disclosed in Huebsch et al., *Circ. Res.*, 77(1), 43–53 (1995). RHE-1A cell spreading on ASD-V modified surfaces were also comparable with RHE-1A spreading on ovalbumin-coupled FN-C/H-V. These results demonstrate that FN-C/H-V retains its biological activity when covalently coupled to material surfaces and may therefore be useful in applications were re-endothelialization is desired (i.e. vascular grafts).

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as each were individually incorporated by reference.

What is claimed is:

1. A solid-phase method of modifying a substrate surface to include a biomolecule, the method comprising:
   (a) providing an immobilized biomolecule comprising a peptide having an $N^{\alpha}$-terminus covalently attached to a support material;
   (b) attaching a photoreactive crosslinking agent comprising at least one photoreactive group to the immobilized peptide at the $N^{\alpha}$-terminus of the peptide to form an immobilized photoreactive analog of the biomolecule;
   (c) removing the photoreactive analog of the biomolecule from the support material; and
   (d) attaching the photoreactive analog of the biomolecule to a substrate surface by activating the photoreactive group of the photoreactive analog.

2. The solid-phase method of claim 1 wherein the photoreactive crosslinking agent is a heterobifinctional photoreactive crosslinking reagent.

3. The solid-phase method of claim 1 wherein the peptide is an adhesion promoting peptide.

4. The solid-phase method of claim 3 wherein the peptide comprises the sequence Trp-Gln-Pro-Pro-Arg-Ala-Arg-Ile (SEQ ID NO:2).

5. The solid-phase method of claim 1 wherein the step of providing an immobilized biomolecule comprises synthesizing the peptide on the support material.

6. The solid-phase method of claim 5 wherein the step of attaching the photoreactive analog of the biomolecule to a substrate surface comprises:
   (a) contacting the photoreactive analog of the biomolecule with a substrate surface; and
   (b) exposing the photoreactive analog of the biomolecule to UV radiation.

7. The solid-phase method of claim 6 wherein the substrate comprises a biomaterial.

8. The method of claim 1 wherein the immobilized biomolecule comprises protecting groups, and wherein step (b) further comprises removing the protecting groups after attaching the photoreactive crosslinking agent to the biomolecule, to form the immobilized photoreactive analog of the biomolecule.

9. A method for making a medical device comprising a biomaterial having a biomolecule thereon, the method comprising:
   (a) providing an immobilized biomolecule comprising a peptide having an $N^{\alpha}$-terminus covalently attached to a support material;
   (b) attaching a photoreactive crosslinking agent to the immobilized peptide at the $N^{\alpha}$-terminus of the peptide to form an immobilized photoreactive analog of the biomolecule;
   (c) removing the photoreactive analog of the biomolecule from the support material; and
   (d) attaching the photoreactive analog of the biomolecule to a biomaterial contained by a medical device; the attaching step comprising:
      (i) contacting the photoreactive analog of the biomolecule to the biomaterial; and
      (ii) exposing the photoreactive analog of the biomolecule to UV radiation.

10. The method of claim 9 wherein the photoreactive crosslinking agent is a heterobifinctional photoreactive crosslinking agent.

11. The method of claim 9 wherein the peptide is an adhesion-promoting peptide.

12. The method of claim 9 wherein the step of providing an immobilized biomolecule comprises synthesizing the peptide on the support material.

13. The method of claim 12 wherein the peptide is an adhesion-promoting peptide.

14. The method of claim 13 wherein the peptide has up to about 20 amino acid residues.

15. The method of claim 14 wherein the peptide has the sequence Trp-Gln-Pro-Pro-Arg-Ala-Arg-Ile (SEQ ID NO:2).

16. The method of claim 9 wherein the medical device is a vascular graft.

17. A method of promoting cell adhesion to a biomaterial, the method comprising:
   (a) providing an immobilized adhesion-promoting peptide comprising an adhesion-promoting peptide having an $N^{\alpha}$-terminus covalently attached to a support material;
   (b) attaching a photoreactive crosslinking agent comprising at least one photoreactive group to the immobilized peptide at the $N^{\alpha}$-terminus of the peptide to form an immobilized photoreactive analog of the adhesion-promoting peptide;
   (c) removing the photoreactive analog of the adhesion-promoting peptide from the support material;

(d) attaching the photoreactive analog of the adhesion-promoting peptide to a biomaterial by activating the photoreactive group of the photoreactive analog; and (e) contacting cells with the biomaterial having the adhesion-promoting peptide thereon.

18. A solid-phase method of modifying a substrate surface to include a biomolecule, the method comprising:

(a) providing an immobilized biomolecule comprising a peptide having an active site covalently attached to a support material;

(b) attaching a photoreactive crosslinking agent comprising at least one photoreactive group to the immobilized biomolecule to form an immobilized photoreactive analog of the biomolecule, wherein the photoreactive crosslinking agent is coupled to the peptide at an amino acid group that is not part of the peptide's active site;

(c) removing the photoreactive analog of the biomolecule from the support material; and (d) attaching the photoreactive analog of the biomolecule to a substrate surface by activating the photoreactive group of the photoreactive analog.

19. The solid-phase method of claim 18 wherein the photoreactive crosslinking agent comprises two photoreactive groups.

20. A method for making a medical device comprising a biomaterial having a biomolecule thereon, the method comprising:

(a) providing an immobilized biomolecule comprising a peptide having an active site covalently attached to a support material;

(b) attaching a photoreactive crosslinking agent to the immobilized biomolecule to form an immobilized photoreactive analog of the biomolecide, wherein the photoreactive crosslinking agent is coupled to the peptide at an amino acid group that is not part of the peptide's active site;

(c) removing the photoreactive analog of the biomolecule from the support material; and (d) attaching the photoreactive analog of the biomolecule to a biomaterial contained by a medical device; the attaching step comprising:

(i) contacting the photoreactive analog of the biomolecule to the biomaterial; and (ii) exposing the photoreactive analog of the biomolecule to UV radiation.

21. A medical device of claim 20 wherein the photoreactive crosslinking agent comprises two photoreactive groups.

22. A method of promoting cell adhesion to a biomaterial, the method comprising:

(a) providing an immobilized adhesion-promoting peptide comprising an adhesion-promoting peptide having an active site covalently attached to a support material;

(b) attaching a photoreactive crosslinking agent comprising at least one photoreactive group to the immobilized adhesion-promoting peptide to form an immobilized photoreactive analog of the adhesion-promoting peptide, wherein the photoreactive crosslinking agent is coupled to the adhesion-promoting peptide at an amino acid group that is not part of the peptide's active site;

(c) removing the photoreactive analog of the adhesion-promoting peptide from the support material;

(d) attaching the photoreactive analog of the adhesion-promoting peptide to a biomaterial by activating the photoreactive group of the photoreactive analog; and (e) contacting cells with the biomaterial having the adhesion-promoting peptide thereon.

23. The method of promoting cell adhesion of claim 22 wherein the photoreactive crosslinking agent comprises two photoreactive groups.

* * * * *

UNITED STATES PATENT AND TRADEMARK OFFICE
CERTIFICATE OF CORRECTION

PATENT NO. : 5,853,744
DATED : December 29, 1998
INVENTOR(S) : Mooradian et al.

It is certified that error appears in the above-identified patent and that said Letters Patent is hereby corrected as shown below:

TITLE PAGE:
1st Column, under "Other Publications", in the Albericio et al. entry, delete "Sythesi" and insert --Synthesis--;

1st Column, under "Other Publications", in the 1st C.G. Fields et al. entry, delete "Fluorenylmthoxycarbonyl" and insert --Fluorenylmethoxycarbonyl--;

2nd Column, under "Other Publications", in the Huebsch entry, delete "Tittle Page" and insert --Title Page--;

, 2nd Column, under "Other Publications", in the Sacher entry, delete "Jun. 2-24, 1987)" and insert --Jun. 21-24, 1987)--;

Col. 3, line 33, delete "defied" and insert --defined--;

Col. 3, line 42, delete "finction" and insert --function--;

Col. 4, line 20, delete "ovalburnin" and insert --ovalbumin--;

Col. 6, line 50, delete "5, 814-816" and insert --115, 814-816--;

Col. 9, line 18, delete "C $_{18}$" and insert --$C_{18}$--;

Col. 9, line 33, delete "fimnel" and insert --funnel--;

Col. 9, line 44, delete "finnel" and insert --funnel--;

Col. 11, line 3, delete "ovalburnin" and insert --ovalbumin--;

UNITED STATES PATENT AND TRADEMARK OFFICE
CERTIFICATE OF CORRECTION

PATENT NO. : 5,853,744
DATED : December 29, 1998
INVENTOR(S) : Mooradian et al.

It is certified that error appears in the above-identified patent and that said Letters Patent is hereby corrected as shown below:

Col. 11, line 57, delete "$[M+H]^{+=}1347.6$ Da" and insert --$[M+H]^+ = 1347.6$ Da--;

Col. 13, line 11, delete "$Pet_c$" and insert --$PET_c$--;

Col. 15, line 40, delete "heterobifinctional" and insert --heterobifunctional--;

Col. 16, line 40, delete "heterobifinctional" and insert --heterobifunctional--; and Col. 17, line 34, delete "biomolecide" and insert --biomolecule--.

Signed and Sealed this

Thirteenth Day of June, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear (ii) MOLECULE TYPE: peptide (xi) SEQUENCE DESCRIPTION: SEQ ID NO:1:

Tyr Ile Gly Ser Arg
 1               5

(2) INFORMATION FOR SEQ ID NO:2:

(i) SEQUENCE CHARACTERISTICS:
    (A) LENGTH: 8 amino acids
    (B) TYPE: amino acid
    (C) STRANDEDNESS: single
    (D) TOPOLOGY: linear   (ii) MOLECULE TYPE: peptide   (xi) SEQUENCE DESCRIPTION: SEQ ID NO:2:

Trp Gln Pro Pro Arg Ala Arg Ile
 1               5